(12) United States Patent
Lima et al.

(10) Patent No.: US 10,328,206 B2
(45) Date of Patent: Jun. 25, 2019

(54) AUTOMATIC INJECTION APPLICATOR

(71) Applicant: Augusto Darwin Moreira de Araujo Lima, Ceara (BR)

(72) Inventors: Augusto Darwin Moreira de Araujo Lima, Ceara (BR); Alexssandra Camarco Prado Lima, Ceara (BR)

(73) Assignee: Augusto Darwin Moreira de Araujo Lima, Fortaleza (BR)

( * ) Notice: Subject to any disclaimer, the term of this patent is extended or adjusted under 35 U.S.C. 154(b) by 29 days.

(21) Appl. No.: 15/552,109

(22) PCT Filed: Jun. 22, 2016

(86) PCT No.: PCT/BR2016/000063
§ 371 (c)(1),
(2) Date: Aug. 18, 2017

(87) PCT Pub. No.: WO2017/083945
PCT Pub. Date: May 26, 2017

(65) Prior Publication Data
US 2018/0071457 A1 Mar. 15, 2018

(30) Foreign Application Priority Data
Nov. 17, 2015 (BR) .............................. 020150288263

(51) Int. Cl.
*A61M 5/20* (2006.01)
*A61M 5/32* (2006.01)
(Continued)

(52) U.S. Cl.
CPC ........ *A61M 5/2053* (2013.01); *A61M 5/3204* (2013.01); *A61M 5/3287* (2013.01);
(Continued)

(58) Field of Classification Search
CPC ............ A61M 5/20; A61M 5/24; A61M 5/32; A61M 5/46; A61M 5/427; A61M 5/482;
(Continued)

(56) References Cited

U.S. PATENT DOCUMENTS 3,720,211 A * 3/1973 Kyrias .................... A61M 5/20
604/155
4,617,016 A * 10/1986 Blomberg ............... A61M 5/20
128/DIG. 1

(Continued)

*Primary Examiner* — Nathan R Price
*Assistant Examiner* — Mark Alan Igel
(74) *Attorney, Agent, or Firm* — Fasth Law Offices; Rolf Fasth

(57) ABSTRACT

An automatic applicator of injection is described, which is equipped with a programmable electronic module that activates a first linear motor (ML1) which axially displaces an arm (13) of the proximal end (11) to the fixed head (20) placed at the distal end of the housing (10), said arm (13) which compresses a cartridge (15) fitted in the chamber (12) formed between the head (20) and the free end of the arm (13) so as to gradually expel the fluid stored in the cartridge; and a second linear motor (ML2) actuated concurrent with the first linear motor (ML1), said second linear motor (ML2) retreating an arm (60) with a dragger (61) which slides axially a suction chamber (30) toward the intermediate portion of the housing (10) and contiguous to the outer surface of the inner chamber (12), gradually exposing the needle tip (50) for application of the injection. The equipment is also equipped with a motor (63) which vibrates the suction chamber (30), tightly sealed, inside which air is removed by a suction pump creating a vacuum for the suction of the mucous against the needle.

1 Claim, 5 Drawing Sheets

(51) Int. Cl.
*A61M 19/00* (2006.01)
*A61M 5/24* (2006.01)
*A61M 5/315* (2006.01)

(52) U.S. Cl.
CPC ..... *A61M 19/00* (2013.01); *A61M 2005/2411* (2013.01); *A61M 2005/31588* (2013.01); *A61M 2202/048* (2013.01)

(58) Field of Classification Search
CPC .. A61M 5/3204; A61M 5/2053; A61M 19/00; A61M 19/19; A61M 2202/048; A61M 1/0066; A61M 1/0068
USPC .................................. 604/115–117
See application file for complete search history.

(56) References Cited

U.S. PATENT DOCUMENTS

| | | | | |
|---|---|---|---|---|
| 5,269,762 | A | * | 12/1993 | Armbruster ............. A61M 5/20 604/131 |
| 5,368,572 | A | * | 11/1994 | Shirota .................. A61M 5/20 604/154 |
| 5,647,851 | A | * | 7/1997 | Pokras .................... A61M 5/20 604/131 |
| 6,669,664 | B2 | * | 12/2003 | Slate ....................... A61M 5/20 604/68 |
| 2003/0114796 | A1 | * | 6/2003 | Schmidt ............ A61B 17/3478 604/158 |

* cited by examiner

Section A-A

Fig. 3C  Detail B

AUTOMATIC INJECTION APPLICATOR

PRIOR APPLICATIONS

This is a US national phase patent application that claims priority from PCT/BR2016/000063 filed 22 Jun. 2016, that claims priority from Brazilian Patent Application No. BR1020150288263, filed 17 Nov. 2015.

FIELD OF INVENTION

The present invention describes an automatic injection applicator. More specifically it comprises an automatic injection applicator provided with an electronic module which triggers a motor for cartridge compression in order to release the liquid into the needle, in parallel to the triggering of a second motor which moves a suction chamber which surrounds the needle so as to expose the needle for the application.

BACKGROUND OF THE INVENTION

A limiting agent of success in the field of drug application, especially in Anesthesiology it is the very means of administering anesthetics. Surveys are conducted in order to discover more effective and less toxic local anesthetic and to improve the equipment used for the application of the drug.

Much of the discomfort generated by the needles is due to its improper handling, however, these instruments have real limitations that make them liable to induce pain.

The mostly used syringe in health care is the aspiration, cartridge type, metal, of breech loading, traditionally called carpule, which, being manual, requires from the professional the condition to introduce the needle with extreme lightness, inject the anesthetic liquid very slowly, but in opposition and simultaneously press the plunger with strength to achieve the penetration of the liquid, especially on certain sites where the tissue is very rigid, such as the subperiosteal region, for instance. The size and cold aspect of the metal associated with the excessive pressure on the syringe plunger, causing very rapid ejection of the anesthetic and/or rapid penetration of the needle end up causing varying degrees of discomfort in individuals.

The state of the art discloses more complex devices for local anesthesia to replace the conventional model. For example, syringes which do not require the use of needle, injecting the anesthetic under high pressure, those that electronically control the release of the anesthetic liquid flow, and plastic syringes, smaller and lighter.

In the 70's a syringe was developed, which was capable to automatically control the anesthetic administration rate, allowing a continuous and regular flow of local anesthetic [HODOSH, M; COMETTA, C.; SHKLAR, G. A new method of injecting local anesthetic painlessly—the Sublimator. Pharmac. Ther. Dent., New York, 2: 65-70, 1975].

In the 80's there came the automatic electronic syringe that in addition to controlling the injection rate also enables the automatic aspiration [MALAMED, S. F. manual of local anesthesia. 3. Ed. Rio de Janeiro, Guanabara Koogan, 1993. 225p].

In Brazil, a similar model, called Control Inject, launched in 1996, performs the electronic control of dosage and drug administration rate, in addition to performing the aspiration, automatically, ensuring continuous and regular flow of the anesthetic solution obtained by the electronic control of the rate and, therefore, the pressure with which the anesthetic is injected into the tissue, providing a more comfortable anesthesia for the patient.

When a fluid is injected into the tissue, there is an increase in the tissue pressure which depends on the speed at which the fluid is injected, the tissue distension capacity and volume of solution injected. An excessive increase in pressure can cause tissue damage resulting in discomfort for the patient during and after the injection. Injections applied with greater volumes and speeds produce higher pressures [ROOD J. P. The pressures created by inferior alveolar injections. Br Dent J 144: 280-282, 1978].

Slow injection of the local anesthetic is one of the means to produce an atraumatic injection. In higher density tissues and with greater adherence to the bone the slow injection is even more important. The rapid injection of the anesthetic solution produces a high tissue pressure that lacerates the soft tissues, causing pain during injection and irritability when the local anesthesic effect ceases [MALAMED, S. F manual de anesthesia local. 3. Ed. Rio de Janeiro. Guanabara Koogan, 1993. 225p]. The slow injection, in contrast, allows the solution to diffuse throughout the normal tissue planes without producing postoperative discomfort [BOMBANA, A. C. Illustrated manual of local anesthesia applied to the dental clinic. $4^{th}$ ed., Sao Paulo, Laboratório Cristália, 1995, p. 31.].

The initial penetration of the needle should be as minimal as possible, just enough so that the bevel of said needle penetrates the skin/mucous to allow the drug used is deposited in the tissues. Still, the penetration of the rest of the needle must happen slowly and gradually allowing the drug's action.

In this context, there are automatic guns fitted with a retractable needle which protrudes externally to the gun's housing as pressure occurs on the plunger for release of the anesthetic.

Document US2005261634 discloses an injection device comprising an elongated body including a container with medication, means for connecting a needle to the container, triggering means capable of injecting a dose of medication after activation, activating means capable of activating said triggering means, a needle shield placed in the referred to body and that can slide between an extended position and a retracted position relative to said body, said needle shield designed in a way that upon penetration of the needle, and dislocated to its retracted position, acts on said activating means, which, in turn, activates said triggering mean and injects a dose.

Document U.S. Pat. No. 6,099,503 discloses a portion of the needle housing that includes a tube mounted so as to slide axially relative to said member of rearming between a rest position, in which it covers the needle of the syringe and a triggering position in which it acts as a triggering element to release the trigger and activate the injection means.

Document 20090326482, by Mark N. Hochman, of Orangeburg, N.Y., US, discloses a device that administers dental anesthetic into intraligamentary tissues characterized by being provided with electronic system, which calculates the tissue pressure and informs the professional, through sound and bright signals, which will serve as delimiters for the professional to identify the tissue in which he is applying the drug.

In April 2007, quoted inventor wrote an article reviewing standards techniques for intraligamentary injection, also referring to the device patented by him [http://www.ncbi.nlm.nih.gov/pubmed/17487044].

Document BR8802885 of the same author, describes a device for puncture control which allows controlling, safely and effectively, the insertion of a needle into the mucous during puncture, so that it penetrates only in areas previously anesthetized by topical medication by suction of the mucous against the needle bezel, to the extent necessary for the anesthetic liquid to be administered.

Document BR102014012252-4, of the FEDERAL UNIVERSITY OF CEARA, ADJUSTABLE DEVICE FOR NEEDLE INSERTION describes a wrap device of needle of syringes, made up of plug-pieces, which protects and hides said needle controlling the level of needle penetration in the object, with adjustable size, allowing the user to adjust the length of the needle that will be inside the device and the extension that will be exposed.

However, the documents of the state of the art disclose applicators wherein the head of the needle is projected jointly design with the plunger compression, exposing the needle to the application, allowing controlling the plunger movement to control the injection fluid, for example. However, the professional still performs manual control of needle penetration into the tissue.

However, the state of the art does not describe an applicator device which allows programming the force/speed of penetration of the needle to overcome the tissue resistance, so that the applicator manually controls the penetration of the needle. In this applicator, it is performed the automatic control of the movement of the suction chamber, which, therefore, controls the penetration of the needle into the mucous, allowing the regular administration, repeatability and force/speed of programmed injection to overcome the tissue resistance and may be associated with other functions, such as release control of drug/anesthetic flow, mucosal suction, head vibration to massage the mucous, among others.

BRIEF DESCRIPTION OF THE FIGURES

FIG. 3C a view highlighting region B, for the best view of the cartridge slot, head and suction chamber.

DETAILED DESCRIPTION OF THE INVENTION

Figure 1:
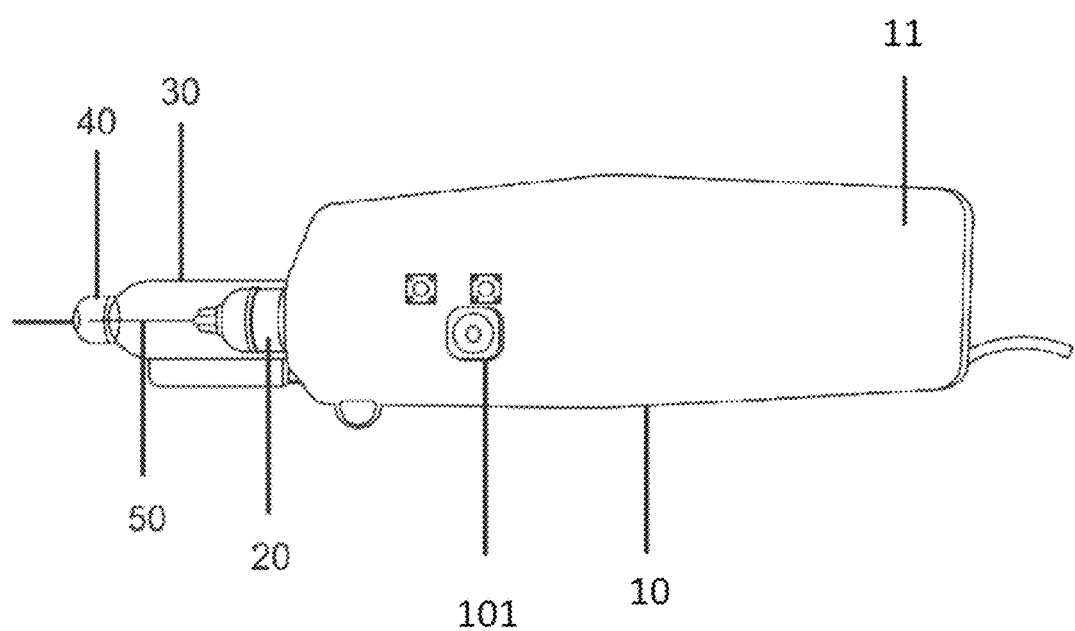
FIG. 1 shows a perspective view of the housing of the automatic applicator of injection.
Figure 2A:
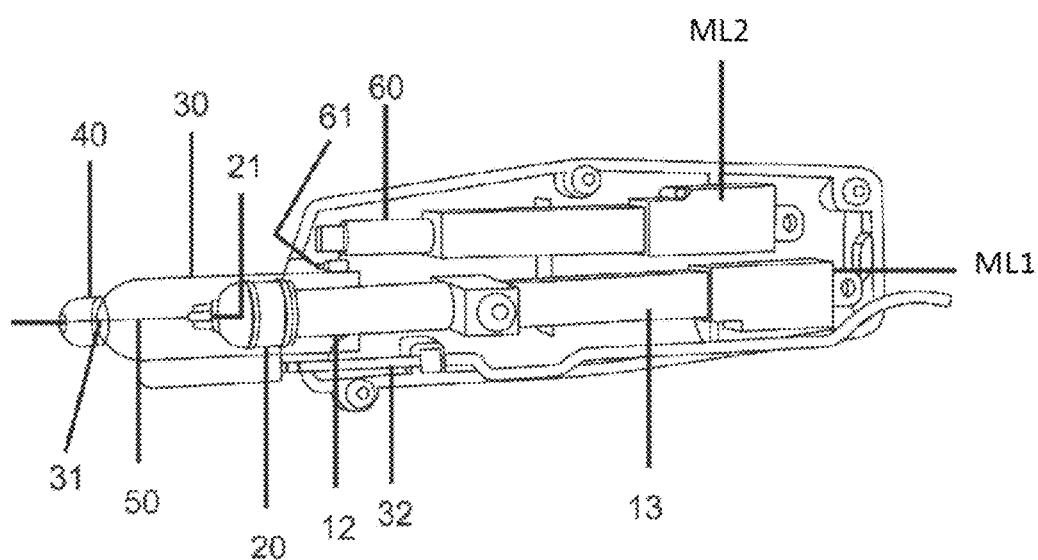
FIG. 2A shows a longitudinal sectional view of the housing of the automatic injection applicator, showing the needle at rest.
Figure 2B:
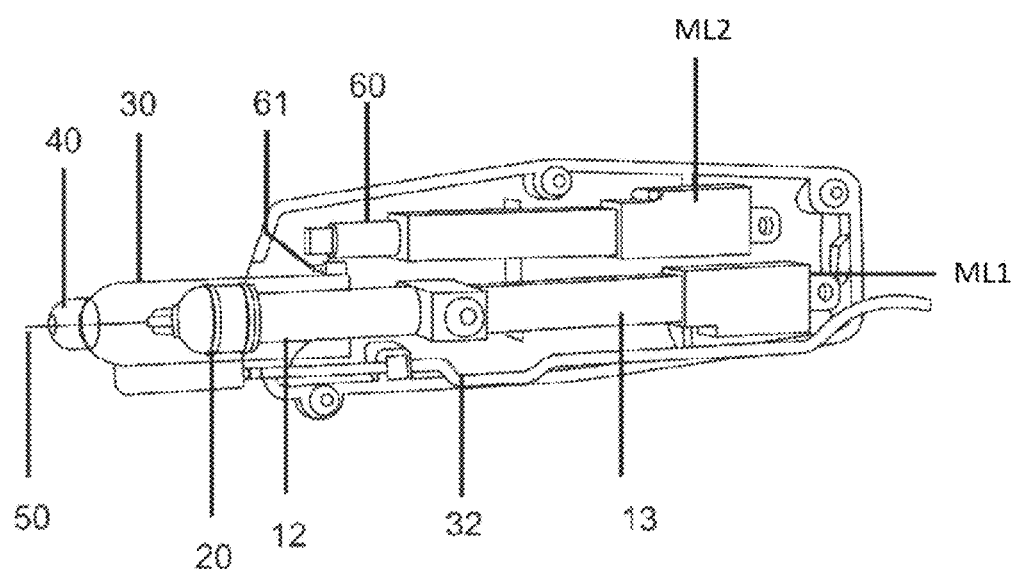
FIG. 2B shows the exposed needle, suitable for application of injection, by displacement of the suction chamber by dragger.
Figure 3A:
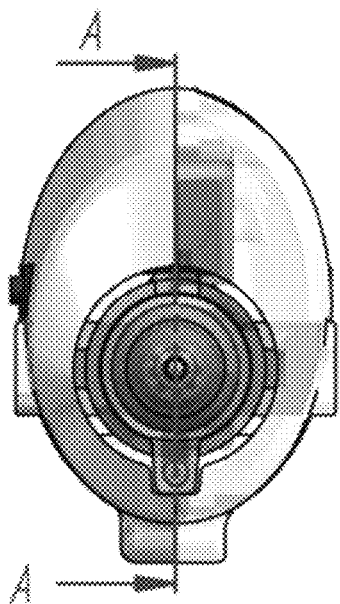
FIG. 3A shows a front view of the applicator.
Figure 3B:
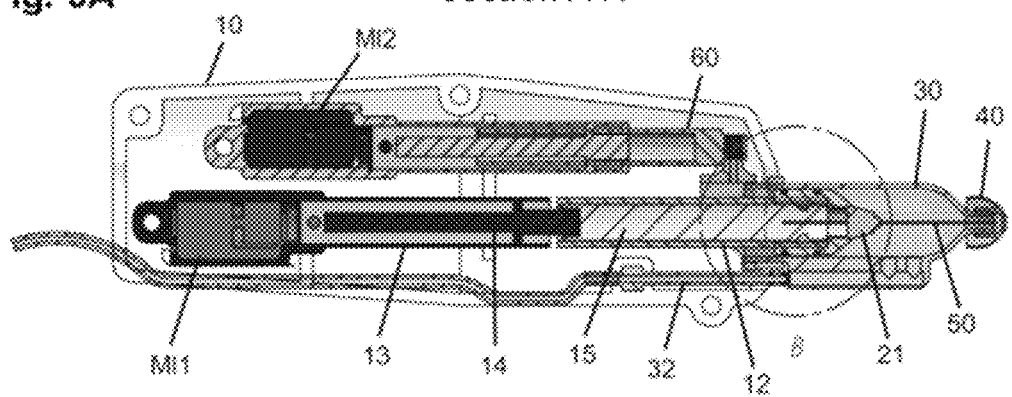
FIG. 3B is a view in section AA, exposing the inner parts, such as cartridge and plunger.
Figure 3D:
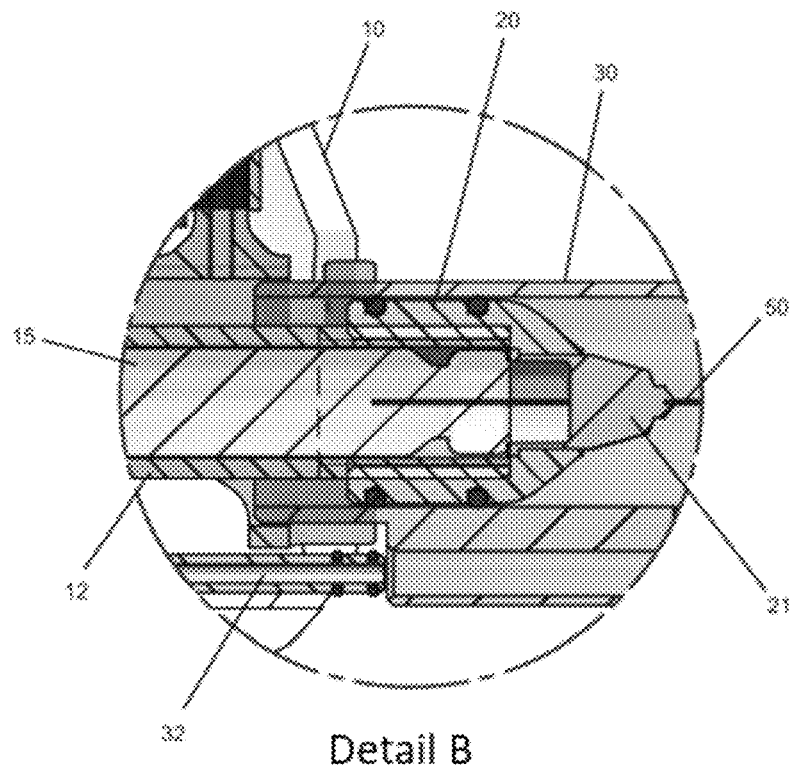
FIG. 3D a view highlighting the vibration mechanism.
Figure 3D:
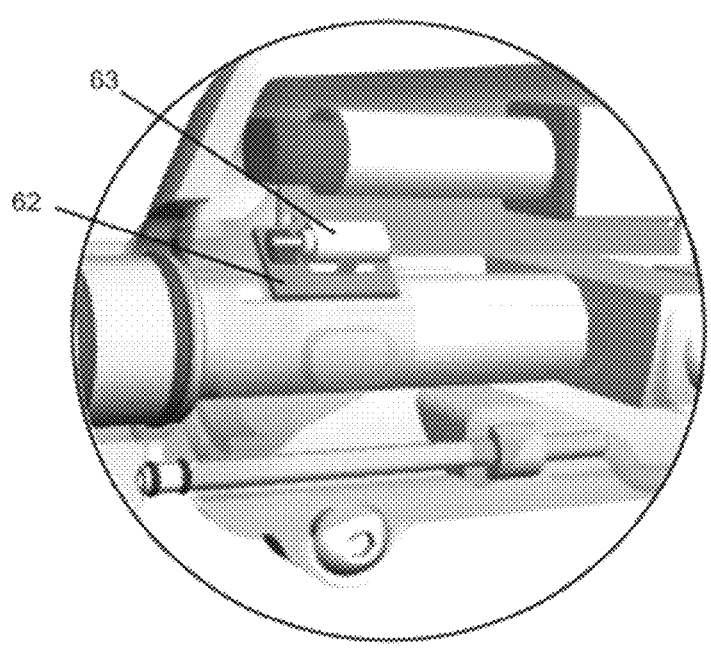

The automatic applicator of the injection, object of the present invention, comprises a housing (10) with an external surface provided with activating buttons (101) of the motors and proximal end with a handle area (11), intermediate region provided with a chamber (12) where an arm is axially displaced (14), enclosed in a rectangular chamber (13) for compression of the anesthetic cartridge (15), packed inside the cylindrical chamber (12) toward a fixed head (20) arranged at the distal end of the housing (10), said fixed head (20) equipped with a needle (50) covered by a suction chamber (30) provided with front opening (31) with a silicone head (40) having an opening (41) which is pierced by the needle end (50) from the suction of the tissue, in order to promote the application of the injection into the patient.

An electronic module equipped with a computer program promotes the activation of a first linear motor (ML1), which extends the arm (14) in the inner chamber (12) where the anesthetic cartridge is previously fixed (15), said arm (13) axially extending from the proximal end (11) to the fixed head (20) at the distal end at a speed controlled by the electronic module, compressing the cartridge (15) so as to gradually expel the fluid stored in said cartridge (15) toward an opening (21) in the fixed head (20) moving the fluid to the needle (50) fixed to said fixed head (20).

Surrounding the suction chamber (30) there is a sleeve (62) on which there is a motor (63), responsible for vibrating this sleeve (62), actuated concurrently with the linear motor (ML1), which consequently makes the suction chamber vibrate (30), vibration that on contact with the mucous, decreases the patient's feeling of pain.

The activation of the first linear motor (ML1) causes, after a few seconds when the vibrational action and the drug have already had some effect, the activation of the second linear motor (ML2), provided with an arm (60) with a dragger (61) axially sliding the suction chamber (30) toward the intermediate portion of the housing (10), said suction chamber (30) moving adjacent the outer surface of the inner chamber (12) to expose the needle end (50) gradually, and the extent to which this movement of the suction chamber occurs (30), the needle (50) finds little resistance in tissues/mucous, which leads to slow and gradual penetration of said needle, and concomitantly occurs drug/anesthetic release/application to the patient, the extent to which the fluid is released by the compression action of the cartridge (15).

The suction chamber (30) comprises an airtight structure provided with a pipe (32), which is connected to a suction pump (not shown) that generates vacuum in said suction chamber (30) in order to suck the skin/mucous from the silicone head (40) for the application of the injection.

While the present invention has been described in accordance with preferred compositions and embodiments, it is to be understood that certain substitutions and alterations may be made thereto without departing from the spirit and scope of the following claims.

We claim:

1. An automatic injection applicator comprising:
a housing with an external surface provided with activating buttons, a proximal end with a handle area, the housing having an internal chamber defined therein in an intermediate region of the housing;
a fixed head placed at a distal end of the housing having a needle covered by a suction chamber provided with a front opening with a silicone head provided with an opening through which the needle is transfixed, a needle end having a third motor in a head inner region, said suction chamber being provided with a pipe connected to a suction pump,
a first linear motor (ML1) in operative engagement with an axially displaceable arm, the axially displaceable arm being movable towards the fixed head placed at the distal end of the housing, said arm being in operative engagement with a compressible cartridge fitted in a chamber formed between the fixed head and a free end of the arm; and a second linear motor (ML2) in operative engagement with an arm and a dragger, the second linear motor (ML2) being triggerable at a time interval after the first linear motor (ML1), a third motor in operative engagement with the suction chamber, the suction chamber being vibrationable by the third motor, the dragger in operative engagement with the suction chamber, the suction chamber being axially slideable towards the intermediate portion of the housing and contiguous to the outer surface of the internal chamber.

* * * * *